United States Patent
Erkamp et al.

(10) Patent No.: US 11,617,860 B2
(45) Date of Patent: Apr. 4, 2023

(54) STEERABLE CATHETER WITH PIEZOELECTRIC TRANSDUCER

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Haytham Elhawary, New York, NY (US); Alvin Chen, Cambridge, MA (US); Shyam Bharat, Arlington, VA (US); Kunal Vaidya, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 413 days.

(21) Appl. No.: 16/970,886

(22) PCT Filed: Feb. 13, 2019

(86) PCT No.: PCT/EP2019/053474
§ 371 (c)(1),
(2) Date: Aug. 18, 2020

(87) PCT Pub. No.: WO2019/162150
PCT Pub. Date: Aug. 29, 2019

(65) Prior Publication Data
US 2020/0376232 A1    Dec. 3, 2020

Related U.S. Application Data

(60) Provisional application No. 62/632,632, filed on Feb. 20, 2018.

(30) Foreign Application Priority Data

Apr. 13, 2018  (EP) .................... 18167284

(51) Int. Cl.
*A61M 25/01* (2006.01)

(52) U.S. Cl.
CPC .... *A61M 25/0147* (2013.01); *A61M 25/0158* (2013.01); *A61M 2025/0166* (2013.01); *A61M 2205/0294* (2013.01)

(58) Field of Classification Search
CPC .......... A61M 25/0147; A61M 25/0158; A61M 2205/0294; A61B 8/445; A61B 8/12
See application file for complete search history.

(56) References Cited

U.S. PATENT DOCUMENTS

| | | | | |
|---|---|---|---|---|
| 4,920,980 A | * | 5/1990 | Jackowski | A61N 1/0565 604/95.04 |
| 6,066,125 A | * | 5/2000 | Webster, Jr. | A61M 25/0136 604/95.04 |

(Continued)

OTHER PUBLICATIONS

PCT/EP2019/053474 WO & ISR, dated Apr. 10, 2019, 13 Page Document.

(Continued)

*Primary Examiner* — Laura A Bouchelle

(57) ABSTRACT

A steerable medical catheter includes a tubular body having a longitudinal axis and a distal portion for insertion into a subject, a first pull wire, a second pull wire, and a piezoelectric transducer. The piezoelectric transducer includes a first electrode and a second electrode. At the distal portion of the catheter the first pull wire and the second pull wire are each mechanically coupled to the tubular body at respective first and second offset positions with respect to the longitudinal axis for imparting a curvature on the distal portion of the catheter. At the distal portion of the catheter the first pull wire is electrically connected to the first electrode of the piezoelectric transducer and the second pull wire is electrically connected to the second electrode of the piezoelectric transducer.

11 Claims, 3 Drawing Sheets

(56) References Cited

U.S. PATENT DOCUMENTS

| | | |
|---|---|---|
| 6,224,587 B1 | 5/2001 | Gibson |
| 7,233,820 B2 | 6/2007 | Gilboa |
| 2004/0176757 A1 | 9/2004 | Sinelnikov et al. |
| 2010/0226903 A1 | 9/2010 | Morris et al. |
| 2014/0255713 A1 | 9/2014 | Devisme et al. |
| 2014/0257130 A1* | 9/2014 | Cao .................. A61B 18/1492 606/41 |
| 2015/0057639 A1 | 2/2015 | Storbeck |

OTHER PUBLICATIONS

Perrella et al: "A New Electronically Enhanced Biopsy System: Value in Improving Needle-Tip Visibility During Sonographically Guided Interventional Procedures"; Department of Radiological Sciences, UCLA School of Medicine, Los Angeles, CA, 1991, pp. 195-199.

Mung et al: "A Non-Disruptive Techology for Robust 3D Tool Tracking for Ultrasound-Guided Interventions"; pp. 153-160.

* cited by examiner

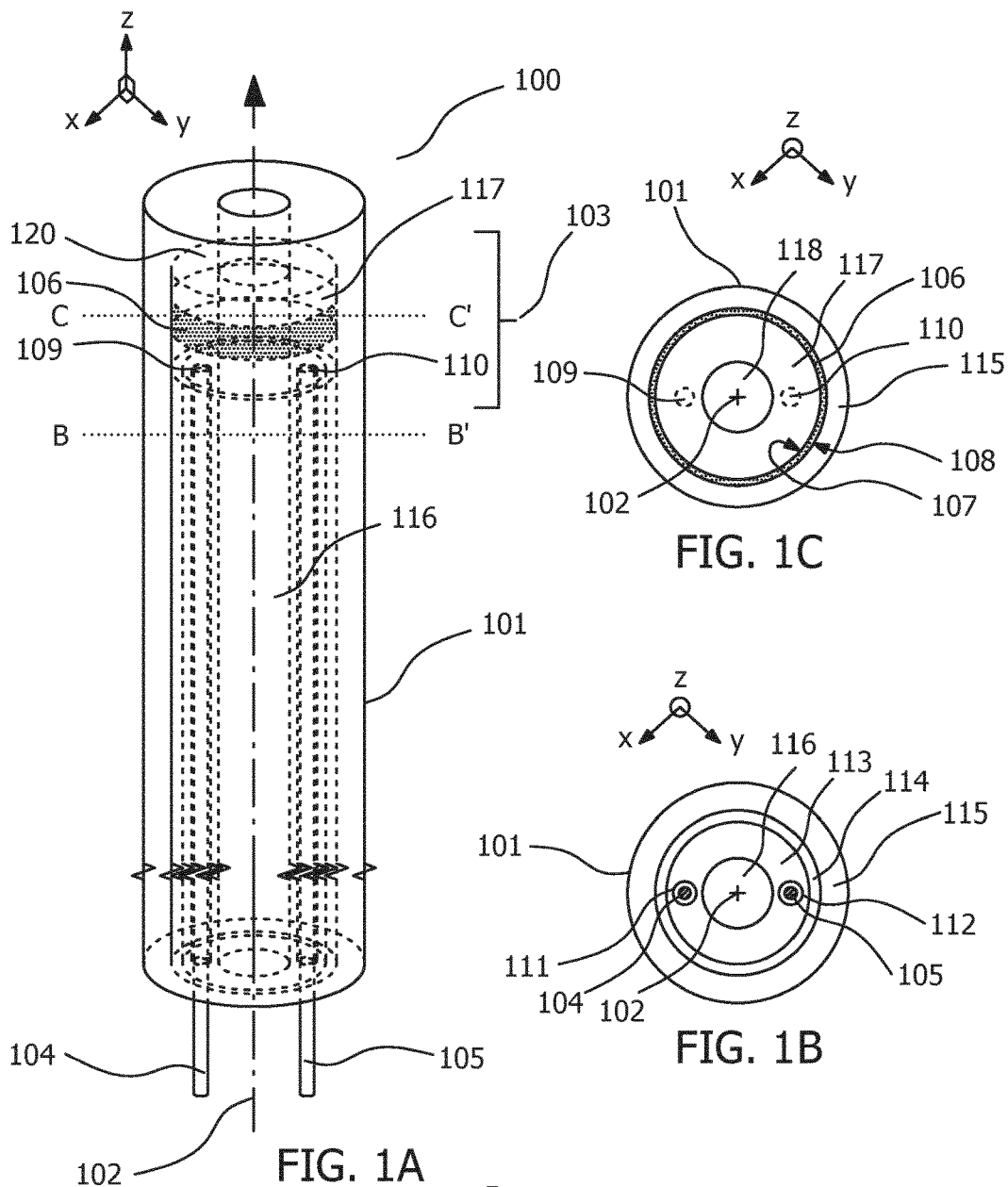
FIG. 1A
FIG. 1B
FIG. 1C
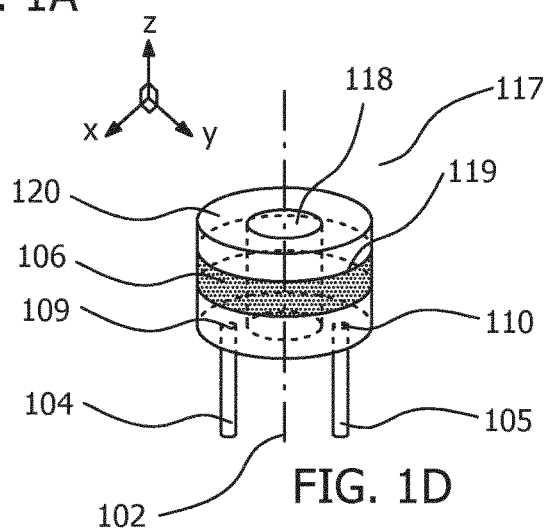
FIG. 1D

STEERABLE CATHETER WITH PIEZOELECTRIC TRANSDUCER

CROSS-REFERENCE TO PRIOR APPLICATIONS

This application is the U.S. National Phase application under 35 U.S.C. § 371 of International Application No. PCT/EP2019/053474, filed on Feb. 13, 2019, which claims the benefit of U.S. Provisional Patent Application No. 62/632,632, filed on Feb. 20, 2018, and European Patent Application No. 18167284.1, filed on Apr. 13, 2018. These applications are hereby incorporated by reference herein.

FIELD OF THE INVENTION

The invention relates to a steerable catheter for use in medical applications. More specifically the invention relates to a steerable catheter that includes a piezoelectric transducer at its distal end. The piezoelectric transducer may be used in various sensing and actuation applications. In one contemplated application the piezoelectric transducer may be used to track a position of a distal end of the catheter respective an ultrasound field of a beamforming ultrasound imaging probe.

BACKGROUND OF THE INVENTION

Steerable catheters are used in numerous medical diagnostic and therapeutic applications. Cardio-vascular, intravascular and pulmonary procedures are three such exemplary applications in which the steerable nature of the catheter is important in navigating the pathways in the body. Steerable catheters are often equipped with one or more so-called pull wires that extend along the length of the catheter to an anchor point at its distal end. The anchor point is offset from the longitudinal axis of the catheter such that by pulling on the pull-wire an axially-offset force imparts a curvature on the catheter's distal end. Such a catheter is described in document U.S. Pat. No. 6,224,587B1.

Catheters in general are increasingly being equipped with transducers for sensing and actuation during medical procedures. Piezoelectric materials are sometimes used in these transducers due to the wide range of transducer functions they offer. Specific, non-limiting examples include the transducing, i.e. conversion of signals from one form of energy to another, of ultrasound, acoustic, vibration, and thermal energy. Such transducers may be used in a wide range of applications including ultrasound-based tracking, ultrasound imaging, blood flow monitoring, heart rate determination, temperature monitoring, and high frequency ultrasound "HIFU" treatment. In one exemplary ultrasound-based tracking application described in a document by Mung, J., et al "A Non-disruptive Technology for Robust 3D Tool Tracking for Ultrasound-Guided Interventions" in Fitchinger, G., Martel, A., Peters, T., (Eds.) MICCAI 2011, Part I, LNCS, Vol. 6891, pp. 153-160, Springer, Heidelberg (2011), an ultrasound-based position determination system is described in which a ultrasound sensor mounted on a needle is used to detect the ultrasound signals from a beamforming ultrasound imaging probe.

An issue faced in such applications is that of making electrical contact with a transducer at the catheter's distal end. Electrical interconnections typically demand an increase in catheter diameter which may limit its navigability. In one solution to this problem the transducer and its interconnect may be temporarily inserted in a free lumen of the catheter and removed prior to the execution of the medical procedure.

SUMMARY OF THE INVENTION

The present invention seeks to provide a steerable medical catheter with improved electrical interconnection to a piezoelectric transducer at its distal end.

Thereto a steerable medical catheter is provided. The steerable medical catheter includes a tubular body having a longitudinal axis and a distal portion for insertion into a subject, a first pull wire, a second pull wire, and a piezoelectric transducer. The piezoelectric transducer includes a first electrode and a second electrode. At the distal portion of the catheter the first pull wire and the second pull wire are each mechanically coupled to the tubular body at respective first and second offset positions with respect to the longitudinal axis for imparting a curvature on the distal portion of the catheter. At the distal portion of the catheter the first pull wire is electrically connected to the first electrode of the piezoelectric transducer and the second pull wire is electrically connected to the second electrode of the piezoelectric transducer.

Advantageously, using the steerable catheter's pull wires to make electrical contact with the piezoelectric transducer restricts the need to increase the catheter diameter to accommodate separate electrical conductors. In so doing, the flexibility of the steerable catheter may be preserved.

According to one aspect the tubular body of the steerable catheter includes a reinforcement layer. The reinforcement layer includes a conductive material that surrounds and thereby electrically shields the first pull wire and the second pull wire.

Further aspects and beneficial effects are described with reference to the appended claims. Moreover, further advantages from the described invention will also be apparent to the skilled person.

BRIEF DESCRIPTION OF THE FIGURES

FIG. 1 illustrates a steerable medical catheter 100 that includes first pull wire 104, second pull wire 105 and piezoelectric transducer 106.

DETAILED DESCRIPTION OF THE INVENTION

Figure 2:
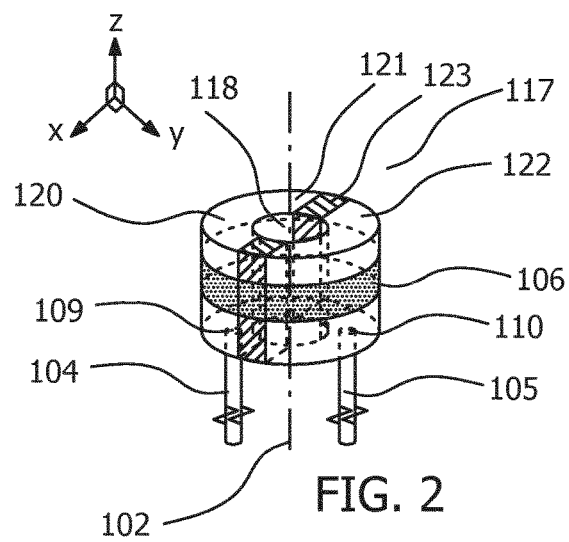
FIG. 2 illustrates a second exemplary steering frame 117.

In order to illustrate the principles of the present invention a steerable medical catheter is described with particular reference to a tracking application. In this exemplary application the position of a cardio-vascular catheter is tracked by means of ultrasound signals detected by a piezoelectric transducer attached to the catheter. It is however to be appreciated that the steerable medical catheter finds application in other medical procedures including intravascular and pulmonary procedures. Moreover, the piezoelectric transducer finds application in sensing and actuation applications beyond position-tracking, such as for example ultrasound imaging, blood flow monitoring, heart rate determination, temperature monitoring, and high frequency ultrasound "HIFU" treatment.

Thereto, FIG. 1 illustrates a steerable medical catheter 100 that includes first pull wire 104, second pull wire 105 and piezoelectric transducer 106. FIG. 1B shows a section through B-B' of the three-dimensional view of FIG. 1A, and FIG. 1C shows a corresponding section through distal end 103 at C-C'. Steerable medical catheter 100 has a tubular body 101 with longitudinal axis 102 and a distal portion 103 for insertion into a subject. Steerable medical catheter 100 is in general flexible, however, distal portion 103 may exhibit a greater degree of flexibility than elsewhere along its length in order to help guide the catheter through the complex pathways in the vasculature. This may be achieved by for example forming distal end 103 from a material having a higher flexibility, or with a thinner diameter, as compared to elsewhere along tubular body 101. Distal end 103 may alternatively include one or more cutout portions, or include a plurality of grooves or holes, for example in a criss-cross pattern, or be shaped in the form of a spiral, along distal end 103 in order to provide a greater degree of flexibility as compared to elsewhere along tubular body 101.

At distal portion 103 first pull wire 104 and second pull wire 105 are each mechanically coupled to tubular body 101 at respective first and second offset positions 109, 110 with respect to longitudinal axis 102 for imparting a curvature on distal portion 103. Pull wires 104, 105 may for example each be attached to the wall of tubular body 101 or to frame 117 as described later. Pull wires 104, 105 are each guided within tubular body 101 by separate lumens 111, 112 that each extend parallel to longitudinal axis 102. The pull wires extend between a tensioning mechanism (not shown) at a proximal end of tubular body 101 and their respective first and second offset positions 109, 110. The pull wire lumens each include an electrically insulating wall that provides electrical isolation. In use, tension on one of the pull wires provides an off-axis force at distal end 103 by means of its offset position with respect to longitudinal axis 102, thereby causing distal end 103 to adopt a curved shape. Thus, by pulling on each of pull-wires 104, 105, a user can navigate changes in direction in the vasculature and ensure a smooth passage of steerable medical catheter 100 to the intended position within the body. Offset positions 109, 110 are illustrated in FIG. 1 as being in diametrically opposite positions respective longitudinal axis 102 and thereby provide for a curvature in each of two opposing directions. Alternative arrangements of the offset positions are also contemplated, such as arranging offset positions 109, 110 with a rotational separation about longitudinal axis 102 that is for example 90 degrees, or indeed any angle between for example 5 degrees and 180 degrees. Moreover, whilst the off-axis radius of each offset position 109, 110 is illustrated as being equal in FIG. 1, these off-axis radii may alternatively be unequal. Alternative arrangements having more than two pull wires are also contemplated.

With continued reference to FIG. 1, piezoelectric transducer 106 includes first electrode 107 and a second electrode 108. At distal portion 103, first pull wire 104 is electrically connected to first electrode 107 and second pull wire 105 is electrically connected to second electrode 108. Advantageously, using the steerable catheter's pull wires to make electrical contact with the piezoelectric transducer restricts the need to increase the catheter diameter to accommodate separate electrical conductors. In so doing, the flexibility of the steerable catheter may be preserved.

Piezoelectric transducer 106 is illustrated in FIG. 1C as a layer that is wrapped around a portion of tubular body 101. First electrode 107 and second electrode 108 are disposed on the major surfaces of this layer, and consequently in the section illustrated in FIG. 1C first electrode 107 and second electrode 108 are disposed, respectively on the inner and outer surfaces of piezoelectric transducer 106. Electrical contact between each electrode 107, 108 and its corresponding pull wire 104, 105 may for example be achieved using a bondwire, electrically conductive glue or paint, and so forth.

Piezoelectric transducer 103 may for example be provided by a layer of Polyvinylidene fluoride, i.e. PVDF, or a layer of PVDF co-polymer such as polyvinylidene fluoride trifluoroethylene (P(VDF-TrFE)) or a layer of PVDF terpolymer such as P(VDF-TrFE-CTFE). In order to facilitate handling and assembly the exemplary PVDF layer may be disposed on a layer of pressure sensitive adhesive, i.e. PSA-coated PET in the form of a transducer strip. Pressure sensitive adhesives form a class of materials that form an adhesive bond upon application of pressure. Sheets of such pressure sensitive adhesives include product 2811CL made by the 3M corporation. These may be supplied as PSA-coated polymer sheets such as product 9019 supplied by the 3M corporation. Piezoelectric transducer 106 may alternatively be made from other soft, or indeed hard piezoelectric materials. Fabrication techniques including the use of dip-coating, molding, sol gel deposition are also contemplated, as is the use of pre-fabricated discrete piezoelectric elements made from polymer materials as well as conventional hard piezoelectric materials such as PZT.

Optionally, and as illustrated in FIG. 1, steerable medical catheter 100 may include central lumen 116. Central lumen 116 may be sized to receive an interventional device such as a catheter or a needle, or another medical tool for performing a procedure at the distal end of medical catheter 100. In a preferred construction, tubular body 101 includes inner liner 113, reinforcement layer 114, and outer sheath 115. Inner liner may for example be formed from fluoropolymer materials such as Fluorinated ethylene propylene, i.e. FEP, or Polytetrafluoroethylene, i.e. PTFE. As illustrated, inner liner 113 is preferably in the form of a tube having a cylindrical cross section. Reinforcement layer 114 serves to reinforce tubular body 101 against kinking and ovalisation of the liner during bending and may for example be in the form of a braid or one or more coils, and may be formed from materials such as type 314 or 316 stainless steel, Polyester, and Polyether ether ketone, i.e. PEEK. Outer sheath 115 may for example be formed from materials such as Polyether block amides such as the material known as PEBAX that is trademarked by Arkema, Colombes, France, FEP, Nylon, Polyethylene, Polyurethane, Ethylene tetrafluoroethylene, i.e. ETFE, or PTFE. Inner liner 113, reinforcement layer 114 and outer sheath 115 each extend coaxially along longitudinal axis 102 of catheter 100 such that reinforcement layer 114 is disposed between inner liner 113 and outer sheath 115. Inner liner 113 defines central lumen 116, and this is coaxial with the longitudinal axis 102. Central lumen 116 allows a medical procedure to be carried out at the distal end of catheter 100 when an interventional device inserted therein.

In a preferred construction, at distal portion 103 of catheter 100, first pull wire lumen 111 and second pull wire lumen 112 are each disposed in inner liner 113. Inner liner 113 with lumens 111, 112 may for example be formed in a single extrusion process. Reinforcement layer 114 may optionally include a conductive material. In the construction illustrated in FIG. 1, reinforcement layer 114 surrounds first pull wire 104 and second pull wire 105 and thereby provides electrical shielding.

In some implementations steerable medical catheter 100 includes a steering frame. The steering frame includes a first anchor point disposed at first offset position 109 and a second anchor point disposed at second offset position 110. Moreover, first pull wire 104 and second pull wire 105 are attached, respectively, to the first anchor point and the second anchor point such that the steering frame mechanically couples first pull wire 104 and second pull wire 105 to the tubular body 101. In one exemplary implementation illustrated in particular in FIG. 1D, steering frame 117 has a cylindrical shape. The steering frame may alternatively have other shapes such as a plate, a cap, a bar and so forth. With reference to FIG. 1C and FIG. 1D, steering frame 117 is in this example formed from a unitary piece of material. Pull wires 104, 105 are attached to steering frame 117 at anchor points at corresponding offset positions 109, 110. In order to provide electrical isolation between pull wires 104, 105 steering frame 117 is preferably formed from an electrically insulating material. Polymers and ceramics are examples of suitable materials for steering frame 117. Materials with a high Shore Hardness value are preferred in view of providing a reproducible curve in the catheter's distal portion 103. Acrylonitrile butadiene styrene, i.e. ABS, is a suitable polymer for steering frame 117 in this respect. Optionally, and as illustrated in FIG. 1D, steering frame 117 may include an inner lumen 118 that is arranged coaxially with longitudinal axis 102 of tubular body 101. In so doing, inner lumen 118 may communicate with central lumen 116 to provide a continuous lumen along the length of steerable medical catheter 100. Optionally, and as illustrated in FIG. 1D, steering frame 117 may have a circumference 119 and piezoelectric transducer 106 may be disposed around this circumference. Piezoelectric transducer 106 may alternatively be disposed around a circumference of tubular body 101. Piezoelectric transducer 106 may thereby provide sensing or actuation around the circumference of the steerable medical catheter. Piezoelectric transducer 106 may be form a continuous band around the circumference or include a gap, or include one or more electrically-interconnected sub-elements with a gaps between each sub-element. Moreover, piezoelectric transducer 106 may at least in part be disposed on end face 120 of steering 117 in order to provide sensing or actuation in a corresponding direction.

Steering frame 117 may alternatively be formed from a conductive material. Various metals including stainless steel may be used, and pull wires 104, 105 securely attached thereto by my means of e.g. welding in order to facilitate a strong anchor point. Thereto, FIG. 2 illustrates a second exemplary steering frame 117. The second exemplary steering frame of FIG. 2 may be used in the position of item 117 in FIG. 1A and may be held in place by for example adhesive or friction provided by compressive forces from outer sheath 115. In contrast to frame 117 in FIG. 1, frame 117 in FIG. 2 includes first conductive member 121 and second conductive member 122. The first conductive member and the second conductive member are separated by insulating layer 123. Insulating layer 123 consequently provides electrical isolation between pull wires 104, 105. Insulating layer 123 may for example be provided by an electrically insulating adhesive, a polymer, a dielectric and so forth. Moreover, the first anchor point is disposed on the first conductive member 121 and the second anchor point is disposed on the second conductive member 122. Thus, in general terms, first conductive member 121 is provided by a first portion of a cylindrical shell, and second conductive member 122 is provided by a second portion of a cylindrical shell. The first portion and the second portion are mechanically attached to each other along the axial extent of the steering frame 117 by insulating layer 123 to provide the cylindrical shell. In FIG. 2 the insulating layer extends along longitudinal axis 102 and conductive members 121, 122 are provided by two half-cylinders. Optional inner lumen 118 may also be included in steering frame 117, inner lumen 118 being arranged coaxially with longitudinal axis 102 of tubular body 101. As in FIG. 1, piezoelectric transducer 106 may be disposed around the circumference of steering frame 117.

Figure 3A:
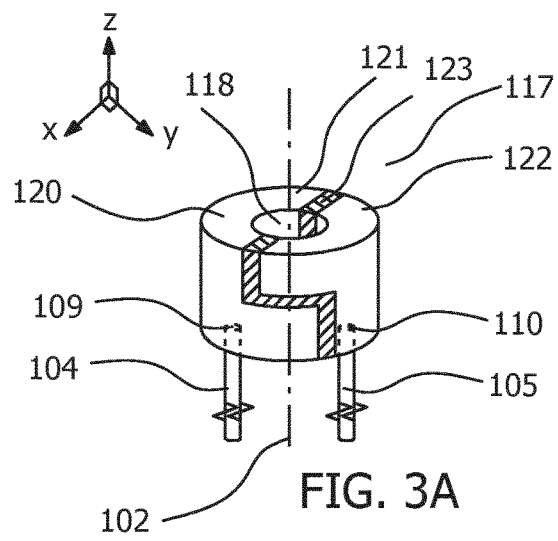
FIG. 3 illustrates a third exemplary steering frame 117.
Figure 3B:
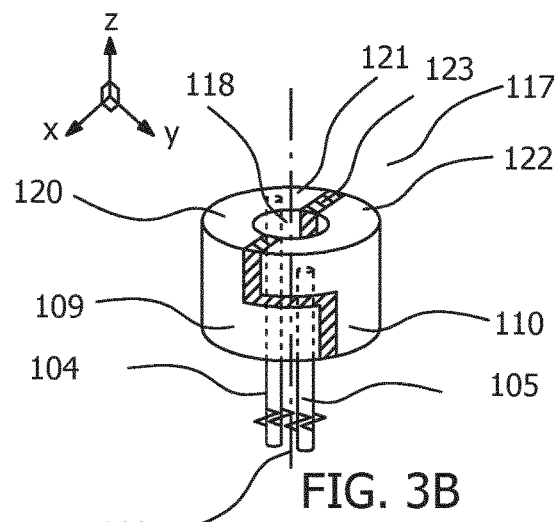

FIG. 3 illustrates a third exemplary steering frame 117. In contrast to steering frame 117 in FIG. 2, first conductive member 121 and second conductive member 122 of the steering frame of FIG. 3 each include an interlocking step along longitudinal axis 102. The interlocking steps provide increased strength along longitudinal axis 102. Piezoelectric transducer 106 is omitted in FIG. 3 for ease of illustration. In FIG. 3A pull wires 104, 105 are both attached at a proximal end of frame 117 whereas in FIG. 3B each pull wire 104, 105 is attached to an interlocking step of its respective conductive member 121, 122 such that tensile force on each pull wire 104, 105 compressively forces the interlocking steps together. This improves the strength of the joint between the conductive members 121, 122. Anchor points 109 and 110 may for example be positioned in end face 120 of each of conductive members 109, 110 in FIG. 3B. Electrical insulation between pull wire 105 that passes through opposite conductive member 121 in FIG. 3B may be achieved by for example providing pull wire 105 with an insulation layer on the wire or on the surface of the lumen, or an epoxy well around pull wire 105.

Figure 4A:
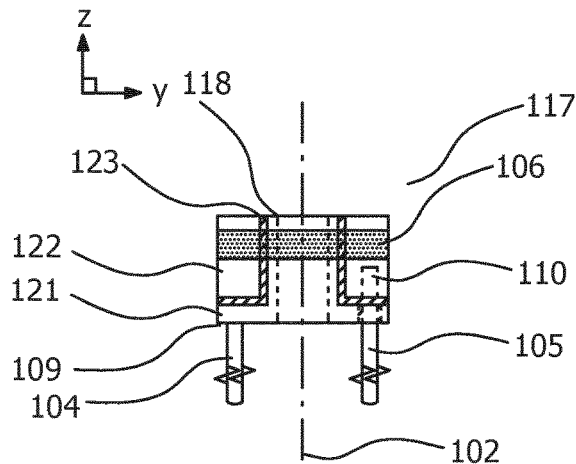
FIG. 4 illustrates a fourth exemplary steering frame 117.
Figure 4B:
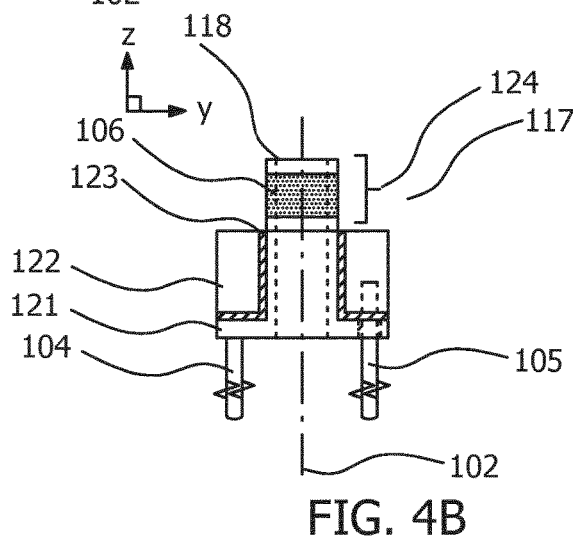

FIG. 4 illustrates a fourth exemplary steering frame 117. Steering frame 117 in FIG. 4 includes first conductive member 121 that is provided by a first cylindrical member, and second conductive member 122 that is provided by a second cylindrical member. The first cylindrical member and the second cylindrical member are arranged coaxially such that the first cylindrical member is within the second cylindrical member. Moreover, insulating layer 123 is disposed between the first cylindrical member and the second cylindrical member. In FIG. 4A, piezoelectric transducer 106 is disposed around the circumference of the second cylindrical member. In an alternative implementation illustrated in FIG. 4B the first cylindrical member includes an extended portion 124 that extends beyond the axial extent of the second cylindrical member and piezoelectric transducer 106 is disposed around the circumference of the first cylindrical member. Anchor points at first and second offset positions 109, 110 are provided, respectively in first conductive member 121 and second conductive member 122. Electrical isolation in the form of e.g. an epoxy well around pull wire 105 may be used to electrically isolate pull wire 105 from first conductive member 121. Alternatively an insulation layer may be provided on pull wire 105 or on the surface of its lumen.

Figure 5:
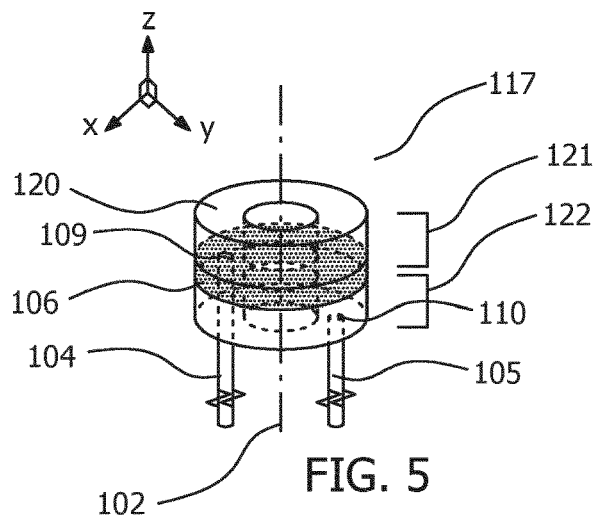
FIG. 5 illustrates a fifth exemplary steering frame 117.

FIG. 5 illustrates a fifth exemplary steering frame 117. Steering frame 117 in FIG. 5 includes first conductive member 121 and second conductive member 122. First conductive member 121 is in the form of a first washer having an axis that is aligned with longitudinal axis 102, and second conductive member 122 is in the form of a second washer having an axis that is aligned with the longitudinal axis 102. Moreover, piezoelectric transducer 106 is sandwiched between the first washer and the second washer such that first pull wire 104 is electrically connected to the first electrode 107 of the piezoelectric transducer 106 via the first washer, and such that second pull wire 105 is electrically connected to second electrode 108 of piezoelectric transducer 106 via the second washer. In so doing the need for additional isolation between conductive members 121, 122 is obviated. Piezoelectric transducer 106 in FIG. 5 may for example be provided by an electrode-coated PVDF layer that extends from a contact region between conductive members 121, 122 onto the circumference of frame 117 or tubular body 101. Alternatively a hard piezoelectric material may be disposed between axially-separated conductive members 121, 122.

It is to be appreciated that whilst the above implementations and examples have been described as having a single piezoelectric transducer, one or more additional piezoelectric transducers may be disposed at axially-separated positions along longitudinal axis 102 of tubular body 101. These additional transducers may optionally be electrically connected in parallel with piezoelectric transducer 106. This provides additional transducer functionality without the need for additional electrical interconnections along the length of the catheter. Such parallel-connected transducers may be provided by for example electrically-interconnecting discrete piezoelectric transducers, or by disposing patterned electrodes on a continuous PVDF layer such that there are electrodes only on both sides of the layer at locations where transducers are desired.

In an alternative implementation to that described above, a steerable medical catheter is disclosed that has one pull wire that is electrically connected to piezoelectric transducer 106, and an electrically conductive reinforcement layer 114. This steerable medical catheter includes a tubular body 101 having a longitudinal axis 102 and a distal portion 103 for insertion into a subject; a pull wire, a piezoelectric transducer 106 comprising a first electrode 107 and a second electrode 108. The tubular body has an inner liner 113, an electrically conductive reinforcement layer 114, and an outer sheath 115. The inner liner 113, the reinforcement layer 114 and the outer sheath 115 each extend coaxially along the longitudinal axis 102 of the catheter 100 such that the reinforcement layer 114 is disposed between the inner liner 113 and the outer sheath 115. The inner liner 113 defines a central lumen 116 that is coaxial with the longitudinal axis 102 for receiving an interventional device. At the distal portion 103 of the catheter 100 the pull wire 104 is mechanically coupled to the tubular body at an offset positions 109 with respect to the longitudinal axis 102 for imparting a curvature on the distal portion 103 of the catheter. At the distal portion 103 of the catheter the pull wire 104 is electrically connected to the first electrode 107 of the piezoelectric transducer 106, and the electrically conductive reinforcement layer 114 is electrically connected to the second electrode 108 of the piezoelectric transducer 106. In so doing the steerable medical catheter is provided with a piezoelectric device that has simplified electrical interconnections.

Figure 6:
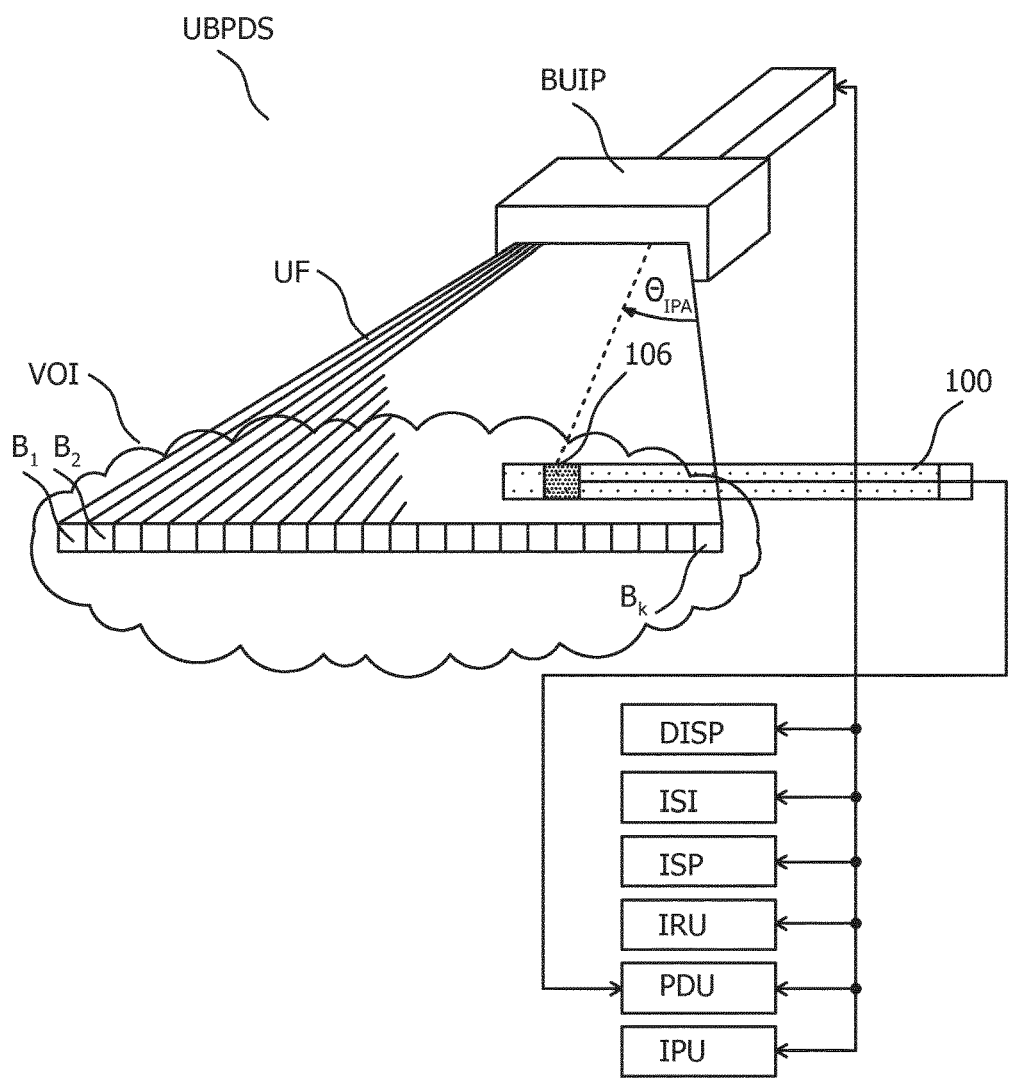
FIG. 6 illustrates an exemplary ultrasound-based position determination system UBPDS in which the steerable medical catheters described herein may be used.

FIG. 6 illustrates an exemplary ultrasound-based position determination system UBPDS in which the steerable medical catheters described herein may be used. Ultrasound-based position determination system UBPDS includes steerable medical catheter 100; a beamforming ultrasound imaging probe BUIP configured to generate an ultrasound field UF, an image reconstruction unit IRU configured to provide a reconstructed ultrasound image corresponding to the ultrasound field UF of the beamforming ultrasound imaging probe BUIP; a position determination unit PDU configured to compute a position of the piezoelectric transducer 116 of the interventional device 110 respective the ultrasound field UF based on ultrasound signals transmitted between the beamforming ultrasound imaging probe BUIP and the piezoelectric transducer 116; and an icon providing unit IPU configured to provide an icon in the reconstructed ultrasound image based on the computed position of the piezoelectric transducer 116.

In FIG. 6, beamforming ultrasound imaging probe BUIP is in communication with image reconstruction unit IRU, imaging system processor ISP, imaging system interface ISI and display DISP. Together, units BUIP, IRU, ISP, ISI and DISP may be provided by a conventional ultrasound imaging system. The units IRU, ISP, ISI and DISP are conventionally located in a console that is in wired or wireless communication with beamforming ultrasound imaging probe BUIP. Some of units IRU, ISP, ISI and DISP may alternatively be incorporated within beamforming ultrasound imaging probe BUIP. Beamforming ultrasound imaging probe BUIP generates ultrasound field UF. In FIG. 6, a 2D beamforming ultrasound imaging probe BUIP is illustrated that includes a linear ultrasound transceiver array that transmits and receives ultrasound energy within an ultrasound field UF which intercepts volume of interest VOI. The ultrasound field is fan-shaped in FIG. 6 and includes multiple ultrasound beams $B_{1 \ldots k}$ that together provide the illustrated image plane. Note that whilst a fan-shaped beam is illustrated in FIG. 6 for the purposes of illustration the invention is not limited to a particular shape of ultrasound field.

In-use the above-described conventional ultrasound imaging system is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted to and detected by beamforming ultrasound imaging probe BUIP. A memory (not shown) may be used to store such programs. The memory may for example store ultrasound beam control software that is configured to control the sequence of ultrasound signals transmitted by and/or received by beamforming ultrasound imaging probe BUIP. Image reconstruction unit IRU, which may alternatively form part of imaging system processor ISP. Image reconstruction unit IRU provides a reconstructed ultrasound image corresponding to ultrasound field UF of beamforming ultrasound imaging probe BUIP. IRU thereby provides an image corresponding to the image plane defined by ultrasound field UF and which thus intercepts volume of interest VOI. The image is subsequently displayed on display DISP. The reconstructed image may for example be an ultrasound Brightness-mode "B-mode" image, otherwise known as a "2D mode" image, a "C-mode" image or a Doppler mode image, or indeed any ultrasound image.

Also shown in FIG. 6 is steerable medical catheter 100 that includes piezoelectric transducer 106. In this exemplary application, piezoelectric transducer 106, and consequently steerable medical catheter 100, may be tracked respective ultrasound field UF based on signals provided by position determination unit PDU and icon providing unit IPU. These units are in communication with one another and units BUIP, IRU, ISP, ISI and DISP, i.e. the conventional ultrasound imaging system as illustrated by the interconnecting arrows. One or more of units PDU and IPU may be incorporated within a memory or a processor of the conventional ultrasound imaging system.

In-use, the position of piezoelectric transducer 106 is computed respective ultrasound field UF by position determination unit PDU based on ultrasound signals transmitted between beamforming ultrasound imaging probe BUIP and piezoelectric transducer 106.

In one configuration piezoelectric transducer 106 is a detector that receives ultrasound signals corresponding to beams $B_{1 \ldots k}$. Position determination unit PDU identifies the position of piezoelectric transducer 106 by correlating the ultrasound signals emitted by beamforming ultrasound imaging probe BUIP with the ultrasound signals detected by piezoelectric transducer 106. Icon providing unit IPU subsequently provides an icon in the reconstructed ultrasound image based on the computed position of piezoelectric transducer 106. More specifically the correlation determines the best fit position of piezoelectric transducer 106 respective ultrasound field UF based on i) the amplitudes of the ultrasound signals corresponding to each beam $B_{1 \ldots k}$ that are detected by piezoelectric transducer 106, and based on ii) the time delay, i.e. time of flight, between emission of each beam $B_{1 \ldots k}$ and its detection by piezoelectric transducer 106. This may be illustrated as follows. When piezoelectric transducer 106 is in the vicinity of ultrasound field UF, ultrasound signals from the nearest of beams $B_{1 \ldots k}$ to the transducer will be detected with a relatively larger amplitude whereas more distant beams will be detected with relatively smaller amplitudes. Typically the beam that is detected with the largest amplitude is identified as the one that is closest to piezoelectric transducer 106. This beam defines the in-plane angle $\theta_{IPA}$ between beamforming ultrasound imaging probe BUIP and piezoelectric transducer 106. The corresponding range depends upon the time delay, i.e. the time of flight, between the emission of the largest-amplitude beam $B_{1 \ldots k}$ and its subsequent detection. The range is determined by multiplying the time delay by the speed of ultrasound propagation. Thus, the range and corresponding in-plane angle $\theta_{IPA}$ of the beam detected with the largest amplitude can be used to identify the best-fit position of piezoelectric transducer 106 respective ultrasound field UF.

In another configuration piezoelectric transducer 106 may be an emitter that emits one or more ultrasound pulses. Such pulses may for example be emitted during tracking frames that are interleaved between the imaging frames of the conventional ultrasound imaging system. In such a tracking frame, beamforming ultrasound imaging probe BUIP may operate in a receive-only mode in which it listens for ultrasound signals originating from the vicinity of ultrasound field UF. Beamforming ultrasound imaging probe BUIP is thus configured as a one-way receive-only beamformer during such tracking frames. Position determination unit PDU identifies from which beam of virtual beams $B_{1 \ldots k}$ the pulse(s) originated by applying delays to the receiver elements of beamforming ultrasound imaging probe BUIP. The delays correspond to each of virtual beams $B_{1 \ldots k}$. As in the detector configuration above, position determination unit PDU may use a correlation procedure that, based on the maximum amplitude and time of flight, identifies the closest beam $B_{1 \ldots k}$ to the position at which the ultrasound signal was emitted, and the corresponding range to piezoelectric transducer 106. Icon providing unit IPU subsequently provides an icon in the reconstructed ultrasound image based on the identified position of piezoelectric transducer 106. Thus, when piezoelectric transducer 106 is an ultrasound emitter, a correlation procedure may again be used to determine the best-fit position of piezoelectric transducer 106 respective ultrasound field UF for each tracking frame.

In another configuration piezoelectric transducer 106 may be configured to act as both a receiver and an emitter, or include a separate receiver and emitter. In this configuration piezoelectric transducer 106 may be triggered to emit one or more ultrasound pulses upon receipt of an ultrasound signal from beamforming ultrasound imaging probe BUIP. In this way the pulse(s) emitted by piezoelectric transducer 106 during an imaging mode are received by beamforming ultrasound imaging probe BUIP appear as an echo in the reconstructed ultrasound at an in-plane angular position, i.e. in an image line, that corresponds to the relevant beam $B_{1 \ldots k}$. Piezoelectric transducer 106 thus appears as a bright spot in the reconstructed image. Position determination unit PDU may subsequently identify this bright spot in the reconstructed image and thus compute a position of piezoelectric transducer 106 respective ultrasound field UF.

It is also to be appreciated that the exemplified beamforming ultrasound imaging probe BUIP is only one example of a beamforming ultrasound imaging system in which steerable medical catheter 100 may be used. Steerable medical catheter 100 also finds application in ultrasound-based position determination systems that include other types of 2D or 3D beamforming ultrasound imaging systems. These may include for example a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe.

Moreover, it is to be appreciated that the piezoelectric transducer also finds application in other sensing and actuation applications in the medical field beyond position determination.

Various example implementations are described below by way of Examples 1-15:

Example 1. Steerable medical catheter (100) comprising:
- a tubular body (101) having a longitudinal axis (102) and a distal portion (103) for insertion into a subject;
- a first pull wire (104);
- a second pull wire (105);
- a piezoelectric transducer (106) comprising a first electrode (107) and a second electrode (108);
- wherein at the distal portion (103) of the catheter (100) the first pull wire (104) and the second pull wire (105) are each mechanically coupled to the tubular body at respective first and second offset positions (109, 110) with respect to the longitudinal axis (102) for imparting a curvature on the distal portion (103) of the catheter;
- and wherein at the distal portion (103) of the catheter the first pull wire (104) is electrically connected to the first electrode (107) of the piezoelectric transducer (106) and the second pull wire (105) is electrically connected to the second electrode (108) of the piezoelectric transducer (106).

Example 2. The steerable medical catheter (100) according to Example 1 wherein the tubular body (101) includes a first pull wire lumen (111) and a second pull wire lumen (112) that each extend parallel to the longitudinal axis (102);
- wherein the first pull wire (104) is disposed in the first pull wire lumen (111);
- wherein the second pull wire (105) is disposed in the second pull wire lumen (112); and
- wherein the first pull wire lumen (111) and the second pull wire lumen (112) each include an electrically insulating lumen wall.

Example 3. The steerable medical catheter (100) according to any one of Examples 1-2 wherein the tubular body (101) comprises an inner liner (113), a reinforcement layer (114), and an outer sheath (115);

wherein the inner liner (113), the reinforcement layer (114) and the outer sheath (115) each extend coaxially along the longitudinal axis (102) of the catheter (100) such that the reinforcement layer (114) is disposed between the inner liner (113) and the outer sheath (115); and wherein the inner liner (113) defines a central lumen (116) that is coaxial with the longitudinal axis (102) for receiving an interventional device.

Example 4. The steerable medical catheter (100) according to Example 3 wherein at the distal portion (103) of the catheter (100) the first pull wire lumen (111) and the second pull wire lumen (112) are each disposed in the inner liner (113).

Example 5. The steerable medical catheter (100) according to Example 4 wherein the reinforcement layer (114) comprises a conductive material for electrically shielding the first pull wire (104) and the second pull wire (105).

Example 6. The steerable medical catheter (100) according to Example 1 further comprising a steering frame (117);

wherein the steering frame (117) comprises a first anchor point disposed at the first offset position (109) and a second anchor point disposed at the second offset position (110); and wherein the first pull wire (104) and the second pull wire (105) are attached, respectively, to the first anchor point and the second anchor point such that the steering frame mechanically couples the first pull wire (104) and the second pull wire (105) to the tubular body (101).

Example 7. The steerable medical catheter (100) according to Example 6 wherein the steering frame (117) further comprises an inner lumen (118), the inner lumen being arranged coaxially with the longitudinal axis (102) of the tubular body (101).

Example 8. The steerable medical catheter (100) according to Example 7 wherein the steering frame (117) comprises a circumference (119); and wherein the piezoelectric transducer (106) is disposed around the circumference of the steering frame.

Example 9. The steerable medical catheter (100) according to any one of Examples 6-8 wherein the steering frame (117) comprises an end face (120); and wherein the piezoelectric transducer (106) is disposed on the end face of the steering frame.

Example 10. The steerable medical catheter (100) according to any one of Examples 6-9 wherein the steering frame (117) comprises a first conductive member (121) and a second conductive member (122), the first conductive member and the second conductive member being separated by an insulating layer (123);

wherein the first anchor point is disposed on the first conductive member (121) and the second anchor point is disposed on the second conductive member (122).

Example 11. The steerable medical catheter (100) according to Example 10 wherein the first conductive member (121) is provided by a first portion of a cylindrical shell, and wherein the second conductive member (122) is provided by a second portion of a cylindrical shell;

wherein the first portion and the second portion are mechanically attached to each other along the axial extent of the steering frame (117) by the insulating layer (123) to provide the cylindrical shell; and wherein the piezoelectric transducer (106) is disposed around the circumference of the cylindrical shell.

Example 12. The steerable medical catheter (100) according to Example 10 wherein the first conductive member (121) is provided by a first cylindrical member, and wherein the second conductive member (122) is provided by a second cylindrical member;

wherein the first cylindrical member and the second cylindrical member are arranged coaxially such that the first cylindrical member is within the second cylindrical member, and such that the insulating layer (123) is disposed between the first cylindrical member and the second cylindrical member; and wherein either:

i) the piezoelectric transducer (106) is disposed around the circumference of the second cylindrical member; or ii) wherein the first cylindrical member includes an extended portion (124) that extends beyond the axial extent of the second cylindrical member and the piezoelectric transducer (106) is disposed around the circumference of the first cylindrical member.

Example 13. The steerable medical catheter (100) according to any one of Examples 6-9 wherein the steering frame (117) comprises a first conductive member (121) and a second conductive member (122), the first conductive member (121) being in the form of a first washer having an axis that is aligned with the longitudinal axis (102) and the second conductive member (122) being in the form of a second washer having an axis that is aligned with the longitudinal axis (102);

wherein the piezoelectric transducer (106) is sandwiched between the first washer and the second washer such that the first pull wire (104) is electrically connected to the first electrode (107) of the piezoelectric transducer (106) via the first washer, and such that the second pull wire (105) is electrically connected to the second electrode (108) of the piezoelectric transducer (106) via the second washer.

Example 14. The steerable medical catheter (100) according to any previous Example further comprising at least a second piezoelectric transducer;

wherein the piezoelectric transducer (106) and the at least a second piezoelectric transducer; are disposed at axially-separated positions along the longitudinal axis (102) of the tubular body (101).

Example 15. The steerable medical catheter (100) according to Example 14 wherein the piezoelectric transducer (106) and the at least a second piezoelectric transducer are electrically connected in parallel.

In summary, a steerable medical catheter has been described. The steerable medical catheter includes a tubular body having a longitudinal axis and a distal portion for insertion into a subject, a first pull wire, a second pull wire, and a piezoelectric transducer. The piezoelectric transducer includes a first electrode and a second electrode. At the distal portion of the catheter the first pull wire and the second pull wire are each mechanically coupled to the tubular body at respective first and second offset positions with respect to the longitudinal axis for imparting a curvature on the distal portion of the catheter. At the distal portion of the catheter the first pull wire is electrically connected to the first electrode of the piezoelectric transducer and the second pull wire is electrically connected to the second electrode of the piezoelectric transducer.

Various implementations and options have been described in relation to the steerable medical catheter, and it is noted that the various embodiments may be combined to achieve further advantageous effects.

The invention claimed is:

1. Steerable medical catheter comprising:
a tubular body having a longitudinal axis and a distal portion for insertion into a subject;
a first pull wire;
a second pull wire;
a piezoelectric transducer comprising a first electrode and a second electrode;
wherein the tubular body includes a first pull wire lumen and a second pull wire lumen that each extend parallel to the longitudinal axis;
wherein the first pull wire is disposed in the first pull wire lumen;
wherein the second pull wire is disposed in the second pull wire lumen; and
wherein the first pull wire lumen and the second pull wire lumen each include an electrically insulating lumen wall;
wherein at the distal portion of the catheter the first pull wire and the second pull wire are each mechanically coupled to the tubular body at respective first and second offset positions with respect to the longitudinal axis for imparting a curvature on the distal portion of the catheter;
wherein at the distal portion of the catheter the first pull wire is electrically connected to the first electrode of the piezoelectric transducer and the second pull wire is electrically connected to the second electrode of the piezoelectric transducer;
wherein the tubular body comprises an inner liner, a reinforcement layer, and an outer sheath;
wherein the inner liner, the reinforcement layer and the outer sheath each extend coaxially along the longitudinal axis of the catheter such that the reinforcement layer is disposed between the inner liner and the outer sheath;
wherein the inner liner defines a central lumen that is coaxial with the longitudinal axis for receiving an interventional device;
wherein at the distal portion of the catheter the first pull wire lumen and the second pull wire lumen are each disposed in the inner liner; and
wherein the reinforcement layer comprises a conductive material for electrically shielding the first pull wire and the second pull wire.

2. The steerable medical catheter according to claim 1 further comprising a steering frame;
wherein the steering frame comprises a first anchor point disposed at the first offset position and a second anchor point disposed at the second offset position; and
wherein the first pull wire and the second pull wire are attached, respectively, to the first anchor point and the second anchor point such that the steering frame mechanically couples the first pull wire and the second pull wire to the tubular body.

3. The steerable medical catheter according to claim 2 wherein the steering frame further comprises an inner lumen the inner lumen being arranged coaxially with the longitudinal axis of the tubular body.

4. The steerable medical catheter according to claim 3 wherein the steering frame comprises a circumference; and
wherein the piezoelectric transducer is disposed around the circumference of the steering frame.

5. The steerable medical catheter according to claim 2 wherein the steering frame comprises an end face; and wherein the piezoelectric transducer is disposed on the end face of the steering frame.

6. The steerable medical catheter according to claim 2 wherein the steering frame comprises a first conductive member and a second conductive member, the first conductive member and the second conductive member being separated by an insulating layer;
wherein the first anchor point is disposed on the first conductive member and the second anchor point is disposed on the second conductive member.

7. The steerable medical catheter according to claim 6 wherein the first conductive member is provided by a first portion of a cylindrical shell, and wherein the second conductive member is provided by a second portion of a cylindrical shell;
wherein the first portion and the second portion are mechanically attached to each other along the axial extent of the steering frame by the insulating layer to provide the cylindrical shell; and wherein
the piezoelectric transducer is disposed around the circumference of the cylindrical shell.

8. The steerable medical catheter according to claim 6 wherein the first conductive member is provided by a first cylindrical member, and wherein the second conductive member is provided by a second cylindrical member;
wherein the first cylindrical member and the second cylindrical member are arranged coaxially such that the first cylindrical member is within the second cylindrical member, and such that the insulating layer is disposed between the first cylindrical member and the second cylindrical member; and wherein either:
i) the piezoelectric transducer is disposed around the circumference of the second cylindrical member; or
ii) wherein the first cylindrical member includes an extended portion that extends beyond the axial extent of the second cylindrical member and the piezoelectric transducer is disposed around the circumference of the first cylindrical member.

9. The steerable medical catheter according to claim 2 wherein the steering frame comprises a first conductive member and a second conductive member, the first conductive member being in the form of a first washer having an axis that is aligned with the longitudinal axis and the second conductive member being in the form of a second washer having an axis that is aligned with the longitudinal axis;
wherein the piezoelectric transducer is sandwiched between the first washer and the second washer such that the first pull wire is electrically connected to the first electrode of the piezoelectric transducer via the first washer, and such that the second pull wire is electrically connected to the second electrode of the piezoelectric transducer via the second washer.

10. The steerable medical catheter according to claim 1 further comprising at least a second piezoelectric transducer;
wherein the piezoelectric transducer and the at least a second piezoelectric transducer; are disposed at axially-separated positions along the longitudinal axis of the tubular body.

11. The steerable medical catheter according to claim 10 wherein the piezoelectric transducer and the at least a second piezoelectric transducer are electrically connected in parallel.

* * * * *